United States Patent [19]

Grooters

[11] Patent Number: 5,197,485
[45] Date of Patent: Mar. 30, 1993

[54] METHOD AND APPARATUS FOR SAMPLING AORTIC PLAQUE

[75] Inventor: Ronald K. Grooters, Fort Washington, Pa.

[73] Assignee: Pilling Co., Fort Washington, Pa.

[21] Appl. No.: 776,825

[22] Filed: Oct. 15, 1991

[51] Int. Cl.$^5$ .............................................. A61B 10/00
[52] U.S. Cl. .................... 128/758; 606/159; 604/122
[58] Field of Search ............... 128/758, 757, 750, 749, 128/DIG. 3; 604/4, 22, 93, 122, 128, 190, 902; 600/16; 606/106, 159; 623/3

[56] References Cited

U.S. PATENT DOCUMENTS

| 3,224,434 | 12/1965 | Molomut et al. | 128/749 |
|---|---|---|---|
| 3,342,175 | 9/1967 | Bulloch | 128/754 |
| 3,526,219 | 9/1970 | Balamuth | 128/752 |
| 3,727,602 | 4/1973 | Hyden et al. | 128/753 |
| 3,785,380 | 1/1974 | Brumfield | 604/902 |
| 3,889,657 | 6/1975 | Baumgarten | 604/22 |
| 4,243,048 | 1/1981 | Griffin | 128/751 |
| 4,249,541 | 2/1981 | Pratt | 128/753 |
| 4,393,879 | 7/1983 | Milgrom | 128/758 |
| 4,655,226 | 4/1987 | Lee | 128/754 |
| 4,680,029 | 7/1987 | Ranford et al. | 604/280 |
| 4,794,928 | 1/1989 | Kletschka | 604/101 |
| 4,815,477 | 3/1989 | McWhorter et al. | 128/766 |
| 4,838,855 | 6/1989 | Lynn | 604/49 |
| 4,857,045 | 8/1989 | Rydell | 604/22 |
| 5,011,490 | 4/1991 | Fischell et al. | 606/159 |
| 5,030,201 | 7/1991 | Palestrant | 604/22 |
| 5,073,168 | 12/1991 | Danforth | 604/167 |
| 5,087,265 | 2/1992 | Summers | 606/159 |

FOREIGN PATENT DOCUMENTS

| 2043843 | 1/1972 | Fed. Rep. of Germany . | |
|---|---|---|---|
| 3045245 | 12/1980 | Fed. Rep. of Germany . | |
| WO8103125 | 11/1981 | PCT Int'l Appl. . | |
| 9001300 | 2/1990 | PCT Int'l Appl. | 604/22 |
| 214022 | 12/1968 | U.S.S.R. | 128/758 |

Primary Examiner—Max Hindenburg
Assistant Examiner—Guy V. Tucker
Attorney, Agent, or Firm—Howson & Howson

[57] ABSTRACT

Apparatus and method for detecting the presence of friable atheromatous deposits in or near the aortic arch of a patient. Fluid aspirated from the aorta in the region of the inner curvature of the transverse arch and the descending aorta through a cannula attached to a handle is drawn by suction through a filter in the handle, and any particulate is trapped for determining the presence of atherosclerotic plaque. A manually operated valve in the handle controls the suction and an elastomeric check valve prevents fluid backflow.

13 Claims, 2 Drawing Sheets

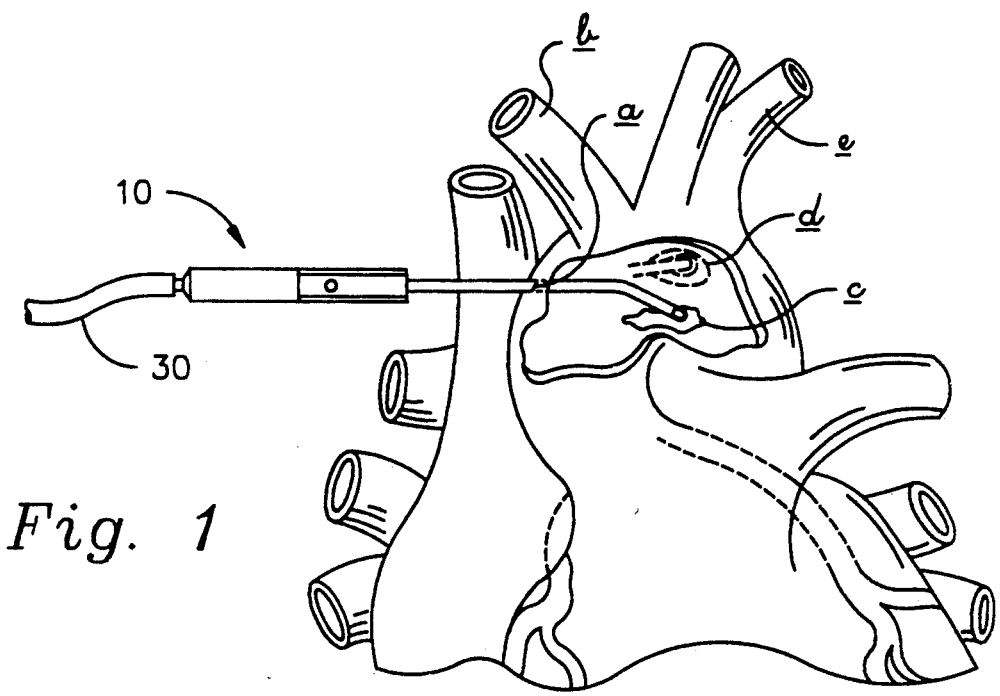
Fig. 1
Fig. 3
Fig. 4
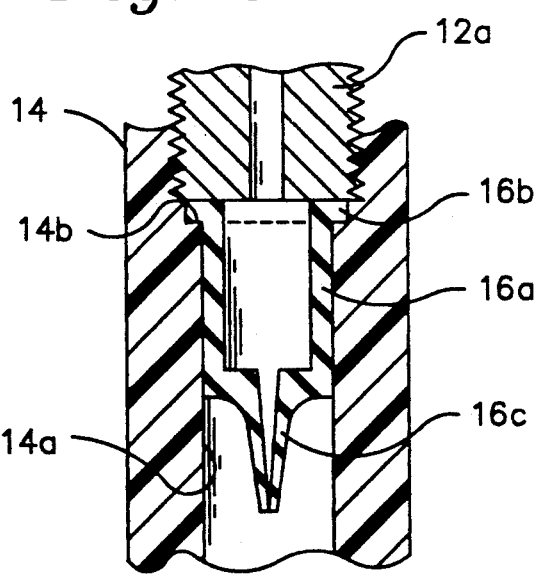
Fig. 5
Fig. 6

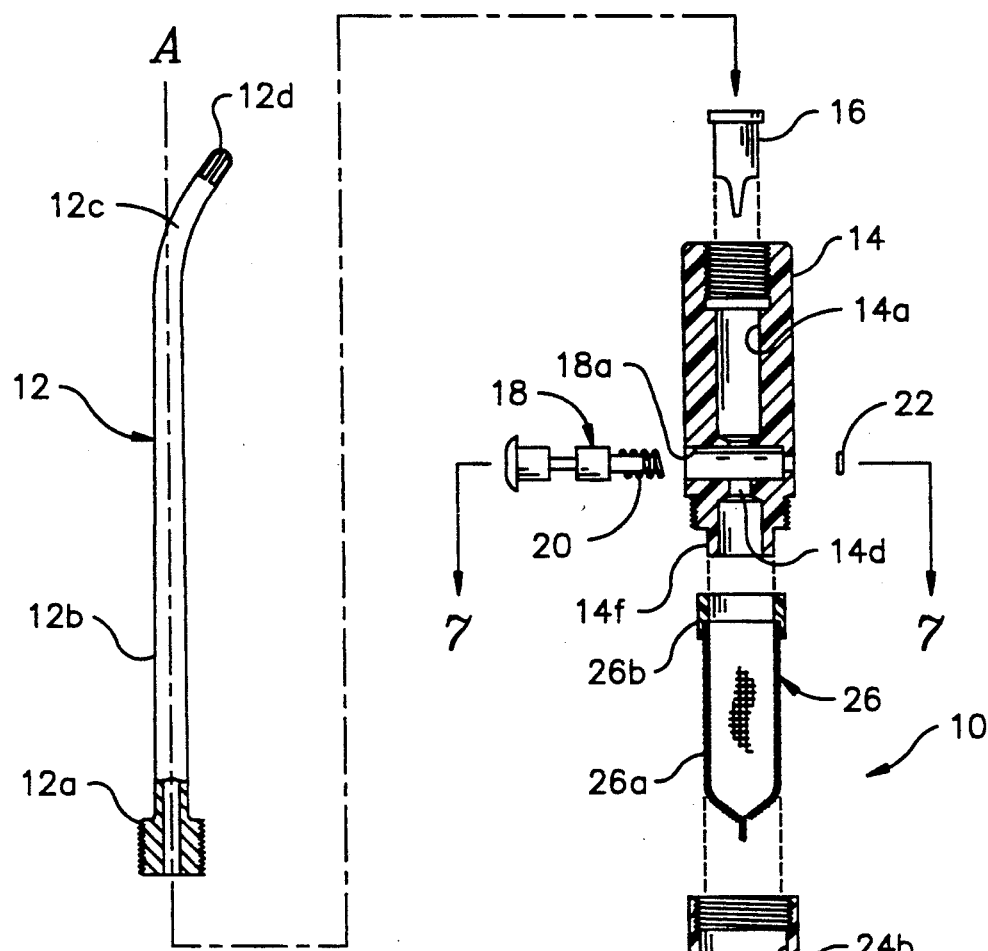
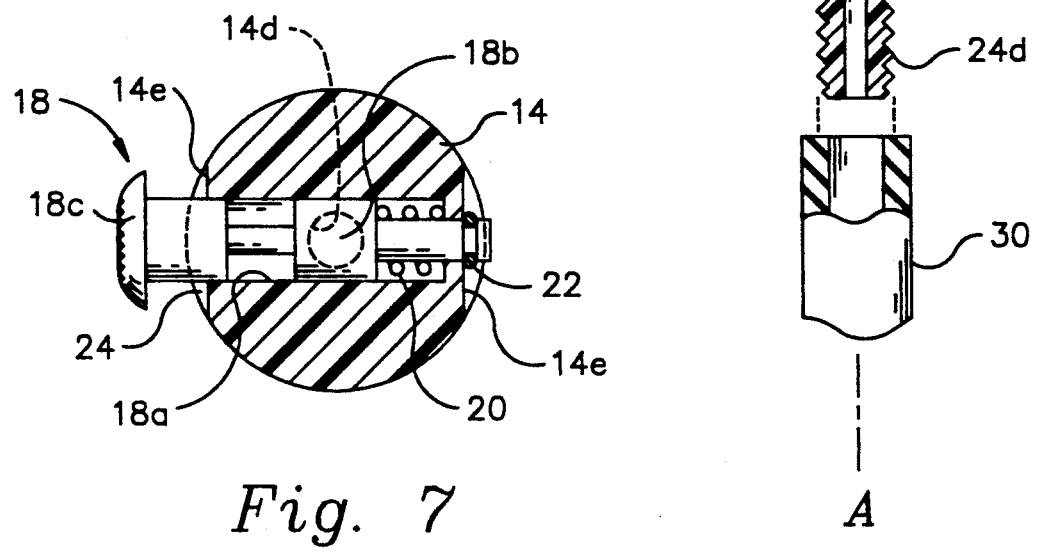

METHOD AND APPARATUS FOR SAMPLING AORTIC PLAQUE

BRIEF SUMMARY OF THE INVENTION

The present invention relates generally to surgical instruments for aspirating non-liquid body materials, and more particularly to methods and apparatus for detecting friable atheromatous deposits in or near the aortic arch.

Myocardial revascularization is a surgical procedure in which saphenous vein bypass grafting to obstructed coronary arteries is performed to help in relieving angina and in reducing the possibility of heart attack. During the surgery a cardiopulmonary bypass is routinely performed in which a heart-lung machine temporarily takes over the function of the heart and lungs. The machine is normally connected to the ascending aorta by a cannula through which blood is perfused thus replacing the natural action of the heart. However, ever since it was first implemented, an uncommon but persistent perioperative complication of neurologic injury, appearing many times as stroke, could occur leading to serious disability or death. Initially, the complication was ascribed to air embolizing either by accident or from what would be unreliable equipment by today's standards.

Prolonged perfusion time exacerbated the neuro injury patterns probably from particulate debris of thrombus and platelets generated within the machine's oxygenator. With cardiopulmonary bypass equipment now improved to almost perfection, these etiological factors are much less a problem, yet neurologic injuries still persisted. Advanced age of the patient, duration of cardiopulmonary bypass, cerebral vascular disease, and atherosclerosis in the vicinity of the aortic arch appeared to be strong predisposing factors along with intraoperative hypotension, carotid disease, air embolus, and postoperative arrest. Of these factors, atherosclerosis of the carotid artery, the ascending aorta, and the transverse aortic arch, singly or combined, have been implicated as among the major risk factors.

Tomography scans and aortograms of patients sustaining massive perioperative embolic strokes revealed large built-up areas of friable atheromatous plaques on the inner curvature of the aortic arch and the descending aorta just distal to the left subclavian artery. This condition appears to be present more often than previously suspected and might be etiologically explained by Bernoulli's theorem. More specifically, "lift" within the vessel wall appears to provide a hemodynamic factor which accelerates the accumulation of atherosclerotic plaque at the inner curvature and three major bifurcations of the arterial tree. Finding no other causes for the neurological injury in observed patients, it is postulated that the velocity of blood flow from the perfusion cannula in the vicinity of the plaques creates a "sandblast" effect, and turbulence which dislodges the plaque from the aortic walls to form particulate debris, allows it to travel through the blood system, and causes significant brain emboli.

This led to a procedure for exploring the aortic arch and descending aorta for friable plaque before inserting the perfusion cannula in the ascending aorta. The procedure is performed prior to revascularization by direct visual inspection through a long incision in the inner curvature of the aortic arch using deep hypothermic circulatory arrest and a clamp on the innominate artery. Hazardous friable debris is then scraped and wiped out, and the arch irrigated clean. See Nishida H., Grooters R. K., Yeager A. A., Soltanzadeh H., Thieman K. C., and Schneider R. F., "Carotid and Aortic Arch Endarterectomy Using Hypothermic Arrest with Coronary Bypass." Ann. Thorac. Surg. 1989; 48:865-6.

This procedure is not only extremely complex and time-consuming, but considerably risky. Moreover, it would have been completely unnecessary if no friable plaque were found.

Accordingly, it is an object of the present invention to reduce the risk of perioperative neurologic injury associated with bypass surgery by detection of friable atheromatous plaque in the aortic wall.

Another object is to provide an aortic sampling apparatus which is suitable for insertion through an arteriotomy made for a perfusion cannula, which is simple in design, and which can be made sufficiently inexpensive to be considered disposable.

Still another object is to provide a sampling apparatus for use in surgery which is capable of collecting friable atherosclerotic plaques and/or cholesterol lodged on the walls of the aortic arch.

A further object is to provide an aortic sampling apparatus which can be readily manipulated to reach the inner curvature of the aortic arch and the descending aorta distal to the left subclavian from an arteriotomy in the ascending aorta near the innominate artery.

A still further object is to provide a method for using an aortic sampling apparatus in the detection of atheromatous debris in the aortic arch prior to initiating cardiopulmonary bypass surgery.

Briefly, these and other objects are achieved by a surgical probe assembly for detecting the presence of friable atheromatous debris deposited in or near the aortic arch. A cannula having a caged tip formed at one end is mounted on a handle at the other end. A suction tube connected to the handle causes fluid to be aspirated through the cannula when a manually operated valve in the handle is opened. A filter trap in the handle captures any particulate carried with the fluid and a check valve prevents reverse flow. The handle can be quickly disassembled to allow the trap to be removed for examining any particulate collected. The distal end of the cannula is arched lengthwise with the tip offset from the longitudinal axis of the handle.

Prior to initiating cardiopulmonary bypass surgery involving aortic perfusion, the cannula of the probe assembly according to the invention is inserted through an arteriotomy made for the perfusion cannula. As suction is applied, the tip of the cannula is passed along the walls of inner curvature of the transverse arch and the descending aorta distal to the left subclavian. The tip is then pulled off the walls, the suction stopped, and the cannula and trap removed and inspected for atherosclerotic debris. If there is none, the bypass surgery may proceed using routine aortic cannulation and perfusion. However, if debris is found, other perfusion sites such as the femoral artery, or other treatment modalities in the protocol, should be considered.

For a better understanding of these and other objects and aspects of the invention, reference will be made to the following detailed description taken in conjunction with the accompanying drawings.

BRIEF DESCRIPTION OF THE DRAWINGS

FIG. 1 is a schematic representation of a sampling apparatus according to the invention in the transverse arch of an aorta, a portion of the arch being cut away to show placement of the apparatus for collecting atherosclerotic debris;

FIG. 2 is an exploded view in longitudinal cross section of the apparatus of FIG. 1;

FIG. 3 is an enlarged side view of a caged tip at the end of the apparatus of FIG. 2;

FIG. 4 is an end view of the caged tip of FIG. 2;

FIG. 5 is an enlarged side view in longitudinal cross section of the apparatus of FIG. 2 in the vicinity of a check valve;

FIG. 6 is an end view of the check valve as view from the bottom of FIG. 5; and

FIG. 7 is an enlarged cross sectional view of the apparatus taken along the line 7—7 of FIG. 2.

DETAILED DESCRIPTION

Referring now to the drawings wherein like characters designate like or corresponding parts throughout the several views, there is shown in FIG. 1 an aortic sampling apparatus 10 inserted through an arteriotomy a made for arterial perfusion at a site next to the takeoff of the innominate artery b on the ascending aorta. The inserted end of the apparatus is shown in solid outline in contact with atherosclerotic deposits c on the inner curvature of the transverse arch of the aorta, and in dotted outline in contact with such deposits d, if any, on the descending aorta distal to the left subclavian artery e.

Referring to FIG. 2, apparatus 10 includes a probe or cannula 12 having a flanged end 12a threadingly engaging one end of a hollow elongate handle section 14 along a longitudinal axis A—A. This allows cannula 12 to be removed from handle section 14 for separate sterilizing or disposal of parts. Alternatively, the proximal end of cannula 12 may be cemented in place to ensure a permanent seal. The length and curvature of cannula 12 provide for optimum accessibility from the site of the aortic incision to either of the aforesaid aortic areas of plaque buildup. A typical cannula configuration for aortic sampling has an overall length of approximately 165 mm measured from handle section 14. The cannula is defined by a straight section 12b elongated along axis an A—A, and a curved section 12c which terminates about 13 mm of axis A—A with a four-strutted cage 12d. The cage insures that the tip of the cannula is free to draw any dislodged plaque quickly into the instrument while preventing large fragments from blocking the cannula passage. It also prevents the opening at the cannula tip from becoming completely blocked by engagement with the interior wall of the aorta.

Referring to FIGS. 5 and 6, the passage of cannula 12 communicates with a cylindrical chamber 14a in handle section 14a which contains an elastomeric check valve 16 having a hollow cylindrical section 16a with a flange 16b at the inlet seated on a shoulder 14b at the inlet of chamber 14a. The valve outlet includes resilient lips 16c tapering together to a normally closed state to prevent backflow of fluid to the cannula 12. This check valve helps to insure against flow of air into the cannula, which could result in the generation of an air embolism, with possibly disastrous consequences.

At the outlet of valve 16, chamber 14a reduces to a narrow bore 14d containing a manually operated slide valve 18 in a cross bore 18a. Referring to FIG. 7, a helical spring 20 and O-ring 22 cooperate to hold a spindle 18b in a position in which it substantially closes off bore 14d. A clearance between bore 18a and spindle 18b insures there will always be a slight amount of flow, further insuring against the passage of air into the blood vessels before the heart pump acts in a vacuum mode. Depressing a knurled end 18c of valve 18 against the force of spring 20 allows fluid to flow freely through passage 14d into a hollow elongated handle section 24 which is threadingly engaged in coaxial alignment with handle section 14 at the end opposite of cannula 12. The exteriors of handle sections 14 and 24 are uniformly circular in cross-section along their combined length but for oppositely disposed flat sides 14e (FIG. 7) which are normal to the length of valve 18 and provide a positive hand grip surface.

The interior of handle section 24 defines a cylindrical chamber 24a containing a removable filter trap 26 with a porosity sufficient to permit blood to flow freely while straining any particulate debris. Trap 26 includes a mesh pouch 26a secured around the inlet to a collar 26b which fits snugly on a boss 14f extending beyond the threaded end of section 14 and which seats against a shoulder 24b at the inlet of chamber 24a. Pouch 26a is substantially square in cross section but for a portion adjacent collar 26b thus providing clearance adjacent the side of chamber 24a for fluid to flow through the sides as well as through the bottom of pouch 26a.

Chamber 24 narrows into a bore 24c formed in a neck end 24d of section 24. A series of concentric ridges about the neck provide a positive grip and seal for an elastomeric suction tube 30 from the heart-lung machine. Handle section 24 is preferably fabricated of transparent plastic to enable visual inspection of fluid flowing through the apparatus.

A method of sampling for aortic plaque with the above-described apparatus according to the invention prior to initiating cardiopulmonary bypass surgery is as follows. Following exposure of the aorta and the heart for contemplated bypass surgery, a double purse string is placed around the site selected for arterial perfusion, usually next to the takeoff of the innominate artery on the ascending aorta, and an arteriotomy is made within the site area. With valve 18 of sampling apparatus 10 closed but for the slight clearance in cross bore 18a, a perfusion pump operating in the suction mode creates a vacuum in the cannula 12 through check valve 16. Cannula 12 is then inserted and the purse string tightened for hemostasis. Sampling starts by pressing the knurled valve 18 inward to increase suction, preferably at a flow rate of 40 cc/kg/min. or approximately one-half of cardiac output. As suction begins, the cage 12d is passed posteriorly along the inner curvature of the aortic arch gently rubbing the wall for about two to three seconds. The handle of the instrument is then rotated to bring the tip of the cannula into engagement with the wall of the descending aorta at a location distal to the left subclavian artery. The procedure continues for another two to three seconds over the descending aorta an estimated four to six centimeters distal to the left subclavian, bringing the cage 12d toward the left subclavian artery. The cage is then pulled off the wall of the descending aorta with suction continuing for another two to three seconds to allow the uptake of any loosened debris. The time required to test both areas of the aorta is approximately ten seconds. Valve 18 is then allowed to close while the tip of cannula 12 is still within the descending aorta. After it is removed, pump suction may be stopped and trap 26 removed for inspection of any yellow particulates suggestive of atherosclerosis. If no particulate or only intima is found in the filter, a perfusion cannula may be installed through the same arteriotomy in order to proceed with the bypass surgery. On the other hand, if the sample reveals particulate of yellow plaque and/or cholesterol crystals, there is risk that such debris will further loosen and cause brain emboli if aortic perfusion were to be used during the bypass surgery. Other arterial perfusion sites, such as a femoral artery, or other alternative treatment modalities in the protocol should then be considered.

Thus, it is apparent that serious complications of stroke can be averted by first performing a diagnostic sampling for atherosclerosis in the vicinity of the aortic arch before cardiopulmonary bypass procedure is initiated. The same arteriotomy contemplated for perfusion cannulation with the heart-lung machine is used for the probe of the present invention. The detection of friable atheromatous plaque harbored in or near the aortic arch and a protocol to avoid perfusing at or in the potentially harmful atherosclerotic pathology is possible. If friable plaque is detected, a different perfusion site or other options may be preferred to avoid dislodging atheromatous debris during perfusion and thereby lower the incidence of stroke and/or the severity of neurologic injury.

It will be understood, of course, that various other changes in the details, steps and arrangement of parts, which have been herein described and illustrated in order to explain the nature of the invention, may be made by those skilled in the art within the principle and scope of the invention as expressed in the appended claims.

I claim:

1. Surgical apparatus for sampling the aorta for atherosclerotic buildup, comprising:

handling means having distal and proximal ends and having a continuous passage extending from said distal end of the handle means to said proximal end thereof;

means at said proximal end of the handle for connecting said continuous passage to a vacuum pump;

cannula means for insertion into the aorta, said cannula means having proximal and distal ends and being connected at its proximal end to said handle, and said cannula means having an inlet opening at its distal end and an internal passage providing communication between said inlet opening and the continuous passage;

means within said continuous passage forming a filter chamber;

removable filter means located in said filter chamber for trapping particulate matter carried with any fluid drawn through said handle by the vacuum pump;

valve means in said continuous passage for controlling the flow of the fluid drawn through said handle; and check valve means within said continuous passage and in the distal direction from said filter chamber, for preventing fluid flow from said filter chamber to said cannula means.

2. Surgical apparatus according to claim 1 wherein said check valve means comprises a cylinder having a passage with an outlet defined by resilient lips tapering together to a normal closed state for preventing flow of fluid from said filter chamber to said cannula means.

3. Surgical apparatus according to claim 1 wherein said cannula is arched on its distal end.

4. Surgical apparatus according to claim 1 wherein said cannula means includes a straight section connected to the distal end of said handle means, said straight section being elongated along an axis, and an arched section extending as a continuation of said straight section in the distal direction from said handle means, said arched section terminating laterally from said axis.

5. Surgical apparatus according to claim 1 wherein said cannula means includes cage means at its distal end for maintaining clearance between its inlet opening and any contacted surface, and preventing the contacted surface from closing off flow of fluid through said inlet opening.

6. Surgical apparatus according to claim 1 wherein said filter chamber has side wall means and wherein said filter means includes an elongated porous pouch having an opening at one end thereof connected to said continuous passage for receiving all of the fluid flowing in the proximal direction, a closure at an opposite end thereof remote from said opening, and a porous tubular part extending between one end and said opposite end, the major part of said porous tubular part being spaced from said side wall of said filter chamber to provide a clearance in said filter chamber for fluid through said porous tubular part.

7. Surgical apparatus according to claim 1 wherein said handle means includes a portion having a non-circular external cross section for providing a positive hand grip surface.

8. Surgical apparatus according to claim 1 wherein said handle means includes first and second mutually connectable parts at an intermediate location along the length thereof, said first and second parts being respectively located toward the proximal and distal ends of the handle means and having longitudinal passages communicating with each other, when said first and second parts are assembled together, to form said continuous passage.

9. Surgical apparatus according to claim 8 wherein said filter means is removable by separation of said first and second parts.

10. Surgical apparatus for sampling the aorta for atherosclerotic buildup, comprising:

handing means having distal and proximal ends and having a continuous passage extending from said distal end of the handle means to said proximal end thereof;

means at said proximal end of the handle for connecting said continuous passage to a vacuum pump;

cannula means for insertion into the aorta, said cannula means having proximal and distal ends and being connected at its proximal end to said handle, and said cannula means having an inlet opening at its distal end and an internal passage providing communication between said inlet opening and the continuous passage;

means within said continuous passage forming a filter chamber;

removable filter means located in said filter chamber for trapping particulate matter carried with any fluid drawn through said handle by the vacuum pump;

valve means in said continuous passage for controlling the flow of the fluid drawn through said handle;

wherein said valve means has an open and a partially closed position, and includes means providing a clearance, when said valve is in its partially closed position, for permitting a limited rate of flow of fluid through said handle, thereby insuring against the passage of air into the aorta.

11. Surgical apparatus according to claim 10 wherein said valve means comprises a cross-bore intersecting said continuous passage, and a spindle movable in said cross-bore along the axis thereof in a direction transverse to the axis of said continuous passage, said spindle having a narrow portion providing a clearance allowing free flow of fluid through said continuous passage when said narrow portion is aligned with said continuous passage, and said spindle also having a wide portion providing a small clearance allowing only a limited flow of fluid through said continuous passage when said wide portion is aligned with said continuous passage.

12. A method of sampling for aortic plague prior to initiating cardiopulmonary bypass surgery, comprising the steps of:

inserting a cannula into the ascending aorta through an incision at a site selected for arterial perfusion;

while applying suction to the cannula, passing the tip of the cannula over a predetermined location with the aorta;

filtering fluids drawn from the aorta through said cannula for determining the presence of aortic plague in trapped particulate matter; and in the absence of plague, inserting a perfusion cannula in the incision for initiating the bypass surgery.

13. A method according to claim 12 wherein said predetermined location is on the inner curvature of the transverse arch of the aorta, and further comprising the step of passing the tip of the cannula over a location in a portion of the descending aorta distal to the left subclavian artery, twisting the cannula to move the tip from one of said locations to the other.

* * * * *

UNITED STATES PATENT AND TRADEMARK OFFICE
CERTIFICATE OF CORRECTION

PATENT NO. : 5,197,485

DATED : March 30, 1993

INVENTOR(S) : Ronald K. Grooters

It is certified that error appears in the above-identified patent and that said Letters Patent is hereby corrected as shown below:

On the title page, Item [75] Inventors:

change the residence of the inventor Ronald K. Grooters to -- West Des Moines, Iowa --.

Column 6, line 50, "handing" should be -- handle --.

Column 8, line 1, "plague" should be -- plaque --.

Column 8, line 11, "plague" should be -- plaque --.

Column 8, line 12, "plague" should be -- plaque --.

Column 8, line 17, "in" should be -- on --.

Signed and Sealed this

Eighteenth Day of January, 1994

Attest:

BRUCE LEHMAN

*Attesting Officer*  *Commissioner of Patents and Trademarks*